(12) United States Patent
Harms et al.

(10) Patent No.: US 9,839,507 B2
(45) Date of Patent: Dec. 12, 2017

(54) SURGICAL IMPLANT

(71) Applicant: Johnson & Johnson Medical GmbH, Somerville, NJ (US)

(72) Inventors: Volker Harms, Hamburg (DE); Jorg Priewe, Kiel (DE)

(73) Assignee: Johnson & Johnson Medical GMBH, Norderstedt (DE)

( * ) Notice: Subject to any disclaimer, the term of this patent is extended or adjusted under 35 U.S.C. 154(b) by 634 days.

(21) Appl. No.: 14/338,363

(22) Filed: Jul. 23, 2014

(65) Prior Publication Data
US 2015/0057762 A1  Feb. 26, 2015

(51) Int. Cl.
| | | |
|---|---|---|
| *A61F 2/02* | (2006.01) | |
| *B29C 43/02* | (2006.01) | |
| *B29C 43/18* | (2006.01) | |
| *B29C 43/20* | (2006.01) | |
| *A61F 2/00* | (2006.01) | |
| *A61L 31/14* | (2006.01) | |
| *B29K 101/12* | (2006.01) | |
| *B29K 105/00* | (2006.01) | |
| *B29L 31/00* | (2006.01) | |

(52) U.S. Cl.
CPC .............. *A61F 2/02* (2013.01); *A61F 2/0063* (2013.01); *A61L 31/148* (2013.01); *B29C 43/021* (2013.01); *B29C 43/18* (2013.01); *B29C 43/203* (2013.01); *A61F 2210/0076* (2013.01); *A61F 2220/0008* (2013.01); *A61F 2220/0033* (2013.01); *A61F 2250/003* (2013.01); *A61F 2250/0031* (2013.01); *A61F 2250/0097* (2013.01); *B29K 2101/12* (2013.01); *B29K 2105/256* (2013.01); *B29K 2995/0056* (2013.01); *B29L 2031/7532* (2013.01)

(58) Field of Classification Search
CPC .. A61F 2/02; A61F 2/0063; A61F 2210/0076; A61F 2220/0033; A61F 2220/0008; A61F 2250/0097; A61L 31/148; B29C 43/18; B29C 43/021; B29C 43/203; B29L 2031/7532; B29K 2101/12; B29K 2105/256
See application file for complete search history.

(56) References Cited

U.S. PATENT DOCUMENTS

| 5,634,931 A * | 6/1997 | Kugel .................. A61F 2/0063 606/1 |
| 2009/0192532 A1* | 7/2009 | Spinnler ............... A61F 2/0063 606/153 |

(Continued)

FOREIGN PATENT DOCUMENTS

| EP | 2593038 | 3/2014 |
| WO | WO 2011/159700 | 12/2011 |
| WO | WO 2012/007578 | 1/2012 |

*Primary Examiner* — Richard Louis
(74) *Attorney, Agent, or Firm* — E. Richard Skula

(57) ABSTRACT

A surgical implant (10) comprises an areal, flexible, porous basic structure (12) having a first face and a second face. At least one resorbable dyed film piece (20) is attached to the basic structure (12) and comprises a plurality of solid protrusions emerging from the dyed film piece (20) in a direction away from the basic structure (12). The at least one dyed film piece (20) is arranged in a shape structure which is asymmetric ("E") in the area of the basic structure (12). Optionally, the implant (10) further comprises an adhesion barrier sheet (16).

23 Claims, 6 Drawing Sheets

(56) References Cited

U.S. PATENT DOCUMENTS

Figure 1:
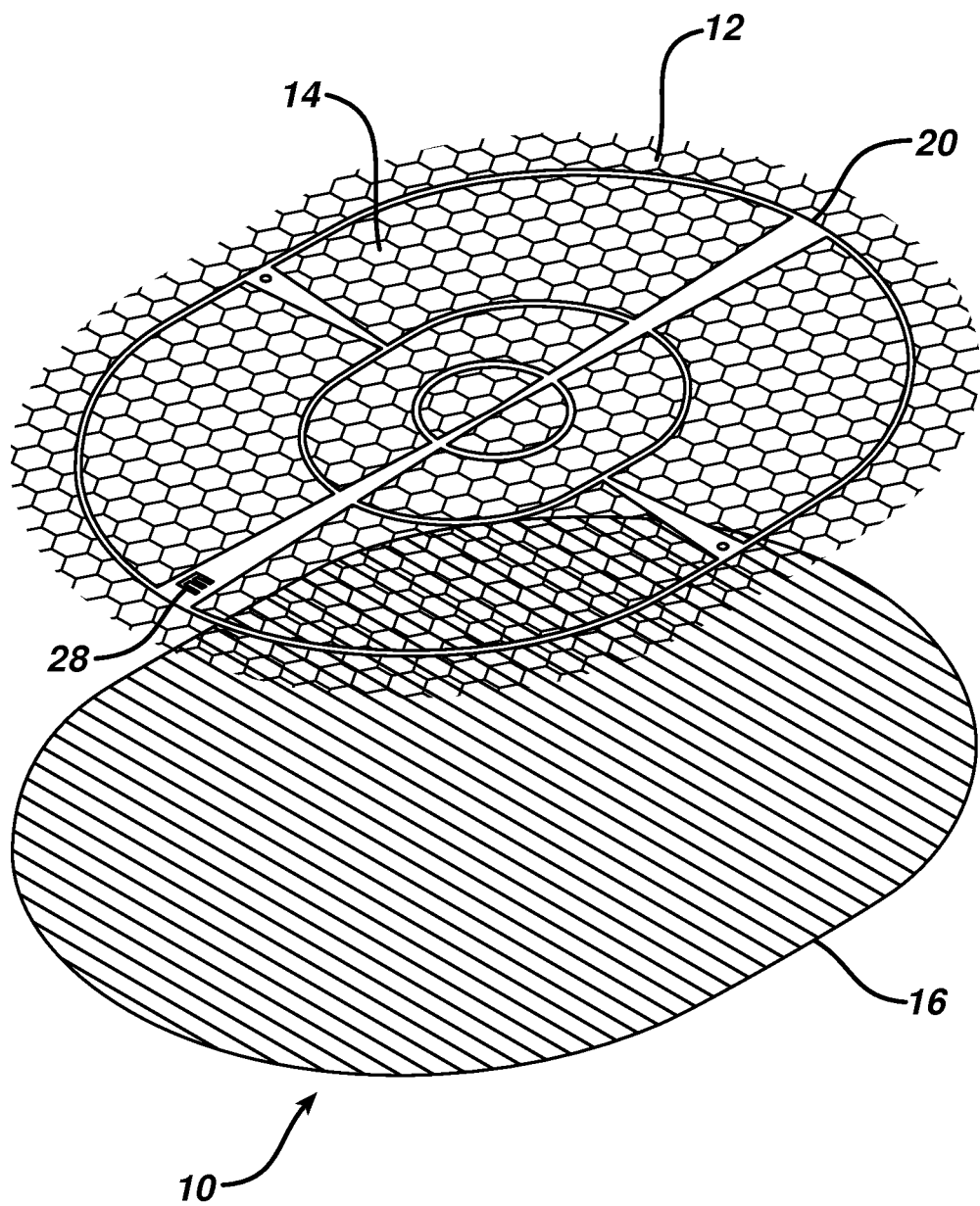

| | | | |
|---|---|---|---|
| 2011/0288566 A1 | 11/2011 | Kubiak | |
| 2011/0307077 A1* | 12/2011 | Pfeiffer | A61F 2/0045 623/23.72 |
| 2013/0158571 A1* | 6/2013 | Meneghin | A61F 2/0063 606/151 |

* cited by examiner

SURGICAL IMPLANT

CROSS REFERENCE TO RELATED APPLICATIONS

This application claims priority from German Patent Application DE102013014295.4 filed Aug. 22, 2013 the disclosure of which is hereby incorporated by reference in its entirety.

The invention relates to a surgical implant, in particular to a tissue reinforcing implant for repair of inguinal hernias and/or ventral/incisional hernias.

Hernia repair is one of the most common surgical procedures, with approximately 6.4 million procedures performed globally every year. Approximately 3.1 million hernias (48%) are repaired with flat mesh annually.

The mesh serving as a surgical implant reinforces the area of the hernia. To achieve a safe fixation, the mesh can be sutured to the bodily tissue close to the hernia. However, the suturing step delays the surgical procedure and can cause post-surgical pain to the patient, e.g. due to nerve damage.

WO 2011/026987 A discloses a prosthetic fabric (mesh) comprising an arrangement of yarns and barbs protruding outwards relative to a face of the fabric. The barbs, which serve as a fixation aid, may be formed from yarns or, as hooks produced from a biocompatible material, are attached to the fabric. The other face of the fabric comprises a microporous layer made of a bio-resorbable material. The barbs are generally sharp due to a cutting process. To decrease the tendency of this product to adhere to itself, e.g. when folded for delivery through a trocar sleeve, the barbs are covered with a coating made of a water-soluble material, which dissolves during the surgical operation. Nevertheless, the handling of the product may be difficult.

For lightweight large-pored meshes with small gripping protrusions on one side, it is often difficult to realize the right face for placement. In particular for meshes having a transparent adhesion barrier film attached to one side, the orientation may be difficult, and a misplacement could be dangerous.

It is known to provide a surgical mesh with markings in order to facilitate placement of the mesh in a surgical procedure.

For example, EP 1 439 796 B1 discloses an areal implant having a mesh-like basic structure and a marking in the central region. A marking line runs through this central marking.

WO 2011/159700 A1 describes a composite implant, which includes an anisotropic surgical mesh having more stretchability along a first axis and less stretchability along a second axis that traverses the first axis. An alignment marker overlies a face of the anisotropic mesh and extends along the first axis. The mesh and the alignment marker are sandwiched between two absorbable anti-adhesion films.

EP 2 593 038 A1 relates to a surgical prosthesis comprising a base fabric and information means designed to guide the surgeon in order to implant the prosthesis in a specified position. The information means include a patch having a color different from that of the base fabric. The patch is provided with barbs projecting from one of its surfaces and can be fixed, by means of the barbs, at a desired position on the surface of the base fabric.

The problem of the invention is to provide a surgical implant, for example for the repair of hernias, which reduces the need for suturing and can be handled during a surgical procedure in an easy, quick and safe way.

This problem is solved by a surgical implant according to claim 1. Claim 18 is directed to a process of manufacturing such a surgical implant. Advantageous embodiments of the invention follow from the dependent claims.

The surgical implant according to the invention comprises an areal, flexible, porous basic structure having a first face and a second face. Moreover, the implant includes at least one resorbable (absorbable) dyed film piece attached to the basic structure (e.g., to its first face) and comprising a plurality of solid protrusions emerging from the dyed film piece in a direction away from the basic structure. The at least one dyed film piece is arranged in a shape structure which is asymmetric in the area of the basic structure.

The basic structure is areal, which means that it is generally flat. It is not necessarily plan, because in principle it might be curved into the third dimension. Moreover, the basic structure is flexible and porous. In advantageous embodiments, it is made of a polymeric material and it comprises a mesh-like structure having pores (e.g. of a size of at least 1 mm), e.g. a surgical mesh, or a porous film. The pores allow the ingrowth of bodily tissue. Such structures are generally well known in the art.

The surgical implant further comprises at least one dyed film piece. Its color is generally well visible in optical contrast to the basic structure or possible other components of the implant. The at least one dyed film piece is arranged in an asymmetric manner. That means, if the surgical implant is flipped over about an axis generally lying in the plane of the basic structure and is observed from the same position as before, the at least one dyed film piece will look different, usually as a mirror image.

The at least one dyed film piece may include just one dyed film piece or a plurality of dyed film pieces.

If it is just one dyed film piece, it comprises a coherent asymmetric shape structure, which means that its shape in the area of the basic structure is asymmetric. In that case, the dyed film piece may extend over a major part of the area of the basic structure, e.g. including its periphery or part thereof, for example in a stripe-like arrangement. Since the dyed film piece locally forms an additional layer fixed to the basic structure, the stiffness to the implant is generally increased by such a design. It is also conceivable that the surgical implant comprises several coherent asymmetric shape structures.

If a plurality of dyed film pieces is provided, the asymmetric shape structure is preferably formed by a plurality of individual dyed film pieces arranged in an asymmetric pattern. In that case, each dyed film piece may have a symmetric shape, but the overall arrangement is in a pattern which is asymmetric. If the dyed film pieces are relatively small, the overall flexibility behavior of the basic structure will not be much affected by the presence of the dyed film pieces.

The surgical implant according to the invention can be designed, e.g., as a hernia implant, as a pelvic mesh, as a breast implant support, or as a repair patch for the dura mater. A particularly preferred application is as a tissue reinforcing implant for repair of inguinal hernias and/or ventral/incisional hernias.

The plurality of solid protrusions emerging from the at least one dyed film piece in a direction away from the basic structure imparts to the implant a self-fixation effect. The protrusions mechanically grip into soft bodily tissue, which results in enhanced resistance to shear forces as well as peel forces. This minimizes the need for additional fixation during the surgical operation, e.g. by means of suturing, with expected less pain risk for the patient and increased speed of the surgical operation. Generally, the surgical implant according to the invention attaches to bodily tissue, but nevertheless can be repositioned during the surgical procedure. Moreover, the surgical implant does not attach to itself, when folded, which much facilitates handling. Generally, the implant can be easily prepared and handled intraoperatively. During the tissue integration period, the implant is securely held in place and mesh migration is prevented. Since the at least one dyed film piece is made of resorbable material, it will be absorbed after some time so that finally no protrusions or barbs will be left in the bodily tissue.

Another advantage of the surgical implant according to the invention also derives from the at least one dyed film piece. Because of its arrangement in an asymmetric shape structure, the at least one dyed film piece provides an optical indication of the correct placement of the implant during open and laparoscopic surgery. Moreover, the orientation (first face of the basic structure facing to the surgeon or facing in opposite direction) of the implant is easily detectable by means of the asymmetric shape structure. This is important because the protrusions have to point in the correct direction and an optional adhesion-preventing layer of the implant (see below) has to face to the correct side as well. Without the optical aid by means of the at least one dyed film piece, it might be difficult to place the implant correctly, it particular when wearing gloves and when the implant is lightweight.

Thus, the at least one dyed film piece has a dual function: It improves attachment to bodily tissue (by means of the protrusions) and it facilitates the correct placement of the implant (because it is dyed and easily visible and because of its asymmetric arrangement). This double effect results in less consumption of material, which is advantageous to the patient, because no extra markers are required in order to indicate the correct position of the implant.

In advantageous embodiments of the invention, the asymmetric shape structure of the at least one dyed film piece defines at least one symbol or a string of symbols. For example, a plurality of dyed film pieces may be arranged as the letters of a word, e.g. a trademark. Alternatively, a word may be represented in inverted form (negative), i.e. by just one dyed film piece in which the parts representing the letters of the word are missing. Similarly, strings of words or combinations of such positives and negatives are conceivable as well. Generally, a string of symbols imparts the required asymmetry. If the string has a meaning, it will be immediately obvious whether it appears in the correct orientation or in mirror form.

In advantageous embodiments of the surgical implant according to the invention, second film pieces (preferably resorbable) are attached to the basic structure (e.g., to its first face), in addition to the at least one dyed film piece, wherein each of the second film pieces comprises at least one protrusion emerging from the respective second film piece in a direction away from the basic structure. The second film pieces are not dyed or are differently dyed, compared to the at least one dyed film piece. The second film pieces (which is to include the case of just one second film piece) are useful if additional attachment area is required. Because of its different color, the at least one dyed film piece is well distinguishable from the second film pieces.

For example, each second film piece can have a size equal to or greater than the size of a pore of a mesh-like basic structure. A second film piece can be shaped, e.g., as a hexagon, rounded hexagon, triangle, rounded triangle, rectangle, rounded rectangle, square, rounded square, circle or ellipse, or it can be cross-shaped, snake-like or spiral-like. The second film pieces may be arranged in a regular pattern. A second film piece may be surrounded by an area of the basic structure free from other film pieces, wherein this area may have a width in the range of, e.g., 1 mm to 10 mm. It is also conceivable that second film pieces are connected to each other via struts, e.g. in pairs (e.g. with one strut between the members of the pair), in small groups or in larger groups. Such struts can be made from the same material as the film pieces. If the struts are relatively narrow, they will form connectors which are not stiff and do not deteriorate the flexibility behavior of the implant.

The total area of all film pieces (i.e., the at least one dyed film piece and the second film pieces) is preferably less than 50% of the area of the first face of the basic structure (e.g. less than a value selected from the following list: 45%, 40%, 35%, 30%, 25%, 20%, 15%, 10%). A total area of all film pieces of about 5% of the area of the first face of the basic structure may already be sufficient to achieve the desired self-fixation effect by means of the protrusions.

The film pieces (i.e., the at least one dyed film piece and the second film pieces) can have a thickness, e.g., in the range of from 5 µm to 250 µm, or in the range of from 10 µm to 200 µm. This is the thickness of the film in an area between protrusions. Generally, the thickness may vary and can be significantly smaller than the thickness of an originally flat film layer used to produce the film pieces including protrusions (see below for examples) because, during the production process, part of the material of the original film layer can be transferred to the protrusions.

In advantageous embodiments of the invention, at least one protrusion is rod-like, pillar-like or mushroom-shaped. A shape defined by a respective body and a respective head, the body emerging from the film piece and terminating in the head, and the head projecting laterally with respect to the body, is a kind of mushroom shape, but somewhat more general. Such mushroom-like protrusions can exhibit a particular effective self-fixation effect.

Preferably, the protrusions have a respective longitudinal axis which emerges from the related film piece at an angle relative to the surface of the film piece in the range of from 50° to 90° or in the range of from 70° to 90°. The protrusions may have a large variety in dimensions, for example, measured along the longitudinal axis of a protrusion, in the range of from 20 µm to 5000 µm or in the range of from 100 µm to 500 µm or of from 20 µm to 400 µm. Typically, the areal density of the protrusions is in the range of from 0.5 protrusions/mm$^2$ to protrusions/mm$^2$ or of from protrusions/mm$^2$ to 4 protrusions/mm$^2$. Of course, the implant may comprise protrusions of different shapes or sizes or protrusions provided in different area densities on respective film pieces. The film pieces and the respective protrusions can be made in one piece, see below for examples of manufacturing processes.

A film may also be attached to the second face of the basic structure. This film can have a variety of properties. For example, it may be provided as single piece, e.g. as a contiguous film covering part of or the whole second face of the basic structure. Or it may be provided as a plurality of film pieces, similar to the second film pieces. Moreover, the film at the second face may be resorbable or non-resorbable. It may comprise protrusions in order to achieve a self-fixation effect, or it may be more or less smooth, without protrusions. If the film has barrier properties, bodily tissue can be prevented from growing into the pores of the basic structure. Adhesion barrier films can be transparent so that it may be generally hard to find out which face of the surgical implant is the first face and which is the second one.

The asymmetric arrangement of the at least one dyed film piece according to the invention provides a clear marker, thus solving this problem.

In another advantageous embodiment of the invention, the effect of film pieces provided with protrusions on both sides (first face and second face) of the basic structure is achieved by one layer of film pieces. In this case, the at least one dyed film piece extends into the pores present in the basic structure, wherein protrusions emerge from the at least one dyed film piece in both directions, away from the first face of the basic structure and away from the second face of the basic structure. The second film pieces or a part thereof can be designed in a similar way.

In particular advantageous embodiments of the surgical implant according to the invention, at least two stripe-like shape structures, each comprising at least one dyed film piece and each defining a string of symbols, are attached to the basic structure (e.g., to its first face). Undyed or differently dyed second film pieces having protrusions may be optionally attached to the basic structure (e.g., to its first face) in a region in between the stripe-like shape structures, if a greater self-fixation effect is desired. For example, the string of symbols can indicate a tradename or a hint to the surgeon, also involving repetitions, so that the marking effect caused by the asymmetry is very obvious and a relatively large area exhibiting a self-fixation effect is provided. The location of the stripe-like shape structures may also give information on the actual position of the implant. As already outlined before, the string of symbols can be presented as a positive (which hardly affects the flexibility of the implant) or as a negative (which generally decreases the flexibility of the implant due to a higher overall thickness of material).

Generally, the film pieces are resorbable because some time after the surgical operation, the self-fixation effect is not needed any more. If the film pieces have disintegrated or have been absorbed at that time, tissue growth at the basic structure and the healing process may be improved. If the basic structure is also resorbable, preferably the film pieces are faster resorbable than the basic structure.

Suitable materials for the resorbable film pieces (i.e. dyed film pieces as well as resorbable second film pieces) are well known in the art. The selection of the film material depends, e.g., on the resorption period. Considering processes of manufacturing the implant according to the invention, it may also depend on the melting temperature of the film material relative to that of the material of the basic structure (see below). For example, the film pieces may comprise poly-p-dioxanone ("PDS"), copolymers of glycolide and ε-caprolactone (e.g., "Monocryl" of Johnson & Johnson Medical GmbH) and/or copolymers of glycolide and lactide (in particular in the ratio 90:10, "Vicryl" of Johnson & Johnson Medical GmbH). Generally, a large variety of synthetic bioabsorbable polymer materials can be used, for example polyhydroxy acids (e.g., polylactides, polyglycolides, polyhydroxybutyrates, polyhydroxyvaleriates), copolymers of lactide and trimethylene carbonate, copolymers of glycolide, lactide and trimethylene carbonate, polycaprolactones, polydioxanones, synthetic (but also natural) oligo- and polyamino acids, polyphosphazenes, polyanhydrides, polyorthoesters, polyphosphates, polyphosphonates, polyalcohols, polysaccharides, polyethers. However, naturally occurring materials such as collagens and gelatine or naturally derived materials such as bioabsorbable gel films cross-linked with omega 3 fatty acids or oxygenized regenerated cellulose (ORC) are conceivable as well.

Suitable materials for the basic structure are also well known in the art. Non-resorbable or very slowly resorbable substances include, e.g., polyalkenes (e.g. polypropylene or polyethylene), fluorinated polyolefins (e.g. polytetrafluoroethylene (PTFE) or polyvinylidene fluoride), polyamides, polyurethanes, polyisoprenes, polystyrenes, polysilicones, polycarbonates, polyarylether ketones (PEEKs), polymethacrylic acid esters, polyacrylic acid esters, aromatic polyesters, polyimides as well as mixtures and/or co-polymers of these substances. Other advantageous materials, many of them being resorbable, include polyhydroxy acids, polylactides, polyglycolides, copolymers of lactide and trimethylene carbonate, copolymers of glycolide, lactide and trimethylene carbonate, polyhydroxybutyrates, polyhydroxyvaleriates, polycaprolactones, polydioxanones, poly-p-dioxanone, synthetic and natural oligo- and polyamino acids, polyphosphazenes, polyanhydrides, polyorthoesters, polyphosphates, polyphosphonates, polyalcohols, polysaccharides, polyethers, cellulose, bacterial cellulose, polyamides, aliphatic polyesters, aromatic polyesters, copolymers of polymerizable substances thereof, resorbable glasses. Particularly advantageous materials include polypropylene (non-resorbable), blends of polyvinylidene fluoride and copolymers of vinylidene fluoride and hexafluoropropene (non-resorbable, e.g. "Pronova" of Johnson & Johnson Medical GmbH) PTFE (non-resorbable; including ePTFE and cPTFE), polysilicones (non-resorbable), poly-p-dioxanone ("PDS", resorbable), copolymers of glycolide and lactide (resorbable), in particular copolymers of glycolide and lactide in the ratio 90:10 ("Vicryl", resorbable), copolymers of glycolide and ε-caprolactone ("Monocryl", resorbable). Biologic materials such as allograft and xenograft are conceivable as well. Generally, the materials suitable for the basic structure may also be considered as materials for an adhesion barrier film (see above).

In summary, the surgical implant according to the invention has a plurality of advantages. The self-fixation properties result in a better comfort to the patient due to a reduced risk of chronic pain that may be associated with suture fixation. The basic structure, e.g. a surgical mesh, is securely held in place during the tissue integration period so that mesh migration is prevented. Afterwards, the film pieces including the protrusions may be absorbed.

Moreover, the time efficiency during the surgical operation is improved. In particular, the surgical implant can be easily prepared and handled intra-operatively. Generally, because of the design of the protrusions, the implant does not tend to adhere to itself when in a rolled or folded state. Thus, the implant is well suitable for laparoscopic placement. It can be forwarded to the site of surgery through a trocar sleeve and easily be unrolled or unfolded thereafter, without sticking to itself. Moreover, although the implant is self-fixating, it allows for repositioning as it is generally possible to peel the implant off from bodily tissue and position it again at a different or displaced location. If its design is flexible enough, the implant will stick well to anatomical structures even if these are not plan. Since it is generally not required to fix the implant by sutures, the surgical procedure tends to be shorter. If nevertheless desired, the implant can be additionally fixated by, e.g., suturing.

The clear marking provided by the asymmetric shape structure of the at least one dyed film piece is another advantage of the surgical implant according to the invention. It permits a reliable, fast and straightforward determination of the correct face which is to point in a certain direction.

If the surgical implant is designed as a soft-tissue implant, e.g. a hernia implant, and is adapted to fix itself at least partially in soft tissue such as muscle or fat, the friction between the surgical implant and the soft tissue can be increased in at least one direction (measured essentially in the plane of the implant) by a factor of 2 or more, compared to a corresponding implant without protrusions.

Generally, the technology of applying dyed film pieces having protrusions could also be used in other medical devices, which have more pronounced three-dimensional configurations, e.g. tubes, stents, vascular implants, hip implants, and so forth. For example, the basic structure (including the film pieces and any additional layers attached thereto) may be formed to a three-dimensional configuration, wherein the surgical implant is designed, e.g., in the form of tube, a vascular implant, a stent, a breast implant, an orthopaedic implant, etc.

A surgical implant according to the invention may be manufactured by using the following steps: providing a mold containing an array of cavities, each cavity having the shape of one protrusion; filling the mold with a fluid material forming the at least one dyed film piece and the protrusions according to a pattern defining the shape structure of the at least one film piece; hardening the fluid material; attaching the at least one dyed film piece to a basic structure, with the protrusions pointing away from the basic structure; removing the mold.

The order of how these steps are listed above does not necessarily represent the sequence in which the steps are executed when the process of manufacturing according to the invention is performed, which is explained in more detail further below.

The mold is preferably flexible and comprises, e.g., silicone, polyurethane, a natural rubber or a synthetic rubber. Silicone, e.g., is very flexible and thermo-stable. The mold is basically planar and provides a surface for forming the film pieces. Extending from this surface, there are cavities, each one having the shape of one protrusion. A silicone mold, e.g., can be manufactured, e.g., by using a mechanically produced master (a positive of the array of protrusions) of a metal or a polymer as a master mold, which is filled with silicone precursors and reacted. Due to the large elasticity of silicone, the master mold can be removed after the reaction is finished, and in use of the mold the mold can be separated from the protrusions formed by the mold, even in case of laterally projecting parts of the protrusions.

In advantageous embodiments of the process, the pattern defining the shape structure of the at least one dyed film piece is determined by a mask placed between the basic structure and the material to be filled in the mold.

The steps of filling the mold with a fluid material which forms film pieces including the protrusions, of hardening the fluid material and of attaching the film pieces to a basic structure, in particular a surgical mesh, may be performed essentially at the same time, for example in the following way:

In this advantageous embodiment, the process uses a layered assembly comprising, in this order: the mold, a surgical mesh (e.g. of polypropylene) as the basic structure, the mask, a sheet of material (e.g. of violet poly-p-dioxanone) for the at least one dyed film piece having a lower melting point than the surgical mesh, and a flexible plate device having a closed surface. The sheet of material is heated to a temperature being higher than its melting point and lower than the melting point of the surgical mesh so that the sheet becomes fluid.

Then the mold and the plate device are pressed towards each other, the plate device serving as a counter-part or kind of anvil, whereby the material for the at least one dyed film piece is transferred through the mask into the mold and, at the same time, embeds the surgical mesh. After decreasing the temperature, the fluid material solidifies (which is the hardening step mentioned above) so that the mold can be removed, due to its high elasticity. In this way, the asymmetric shape structure of the at least one dyed film piece is formed by the mask and firmly connected to the surgical mesh, and the protrusions are formed, all steps occurring virtually simultaneously.

In a variant of the latter embodiment, the initial positions of the surgical mesh and the sheet of material for the at least one dyed film piece are interchanged. In this case, the material for the dyed film piece(s) is transferred into the mold and embedded in the surgical mesh in those areas which are not shielded by the mask.

The flexible plate device can comprise a closed surface. Alternatively, it may be designed as a second mold, which is flexible and contains an array of cavities, each cavity having the shape of one protrusion. This second mold is similar to the other mold and can be used to prepare protrusions on the second face of the mesh to produce a surgical mesh implant comprising protrusions on both faces.

In order to prepare second film pieces and attach them to the surgical mesh in areas being free from the at least one dyed film piece, slightly modified processes can be used. To this end, sheet material for preparing the second film pieces is placed side by side to sheet material used for preparing the at least one dyed film piece so that the respective sheets do not overlap. Otherwise, the processes are as described before.

The mask also defines the shapes and positions of the second film pieces.

Depending on the materials used and the details of the process, the hardening step may be performed by evaporation of a solvent, by cooling (as in the examples above) or by reacting reactants forming the film and the protrusions.

In the following, some aspects of the invention, in addition to those involved in the marking effect of the at least one dyed film piece, are further disclosed in general terms.

EXAMPLES OF APPLICATIONS

Soft tissue repair implants such as surgical meshes are mainly used when a defect or weakness exists in soft tissue or a tissue hole has to be filled or covered:

(a) Ventral and inguinal hernias occur when a tissue, a structure, or part of an organ protrudes through an abnormal opening in the body. It is most commonly associated with the projection of the intestine through a weak point in the abdominal wall. Hernia repair devices could be made in different shapes and from different materials, in the form of flat devices, basically flat but curved devices, pouches, bags or folded into plugs.

(b) Surgical meshes, tapes or slings are used in the field of pelvic disorders like stress urinary incontinence or pelvic organ prolaps. In these applications, there may be a need to place the fabric in contact with the vaginal wall (e.g., a pelvic mesh) or in contact with the urethra such as with the GYNECARE® TVT system from Ethicon, Inc., wherein the inventive assembly might support the locking in certain regions of the tape or mesh.

(c) Durapatches are used after brain surgery to cover and close the dura mater. The dura mater is the tough, inflexible fibrous sheath, which is the outermost of three layers that surround the brain and spinal cord. Commercial grafts are made up of either biologic (includes xenografts and allografts) or synthetic material. The inventive micro-protruded film patches in certain areas on one of the both sides might help to keep the implant in place.

(d) Rotator cuff reinforcement grafts are most often used in cases where existing tissue can no longer be used or treated to support the rotator cuffs functions.

(e) Absorbable pouches are used in the field of trauma surgery as a liver compression device to reduce bleeding, like "Vicryl Mesh bag A".

(f) Grafts in the field of breast reconstruction are used with the "TRAM-flap" procedure, where an autogeneous tissue reconstruction of the breast is performed with the transverse rectus abdominus myocutaneous (TRAM) flap from the chest. The abdominal wall donor site for the muscle flap might develop a potential abdominal wall weakness, bulging, and hernia. To prevent hernia, most surgeons will use a synthetic mesh when closing the abdomen. Fabrics such as absorbable meshes like "Vicryl" mesh or "TiGr matrix" are also used in breast augmentation or reconstruction i.e. in oncoplastic surgery which is defined as a combination of tumor excision, with appropriate margin including lympectomy or mastectomy, and immediate reconstruction of the breast (Koo et al. 2011 "Results from Over One Year of Follow-Up for Absorbable Mesh Insertion in Partial Mastectomy" Yonsei Med J 52(5):803-808, 2011). The inventive devices will help to minimize sutures, tacks or glues.

(g) Soft tissue repair devices are used as a filler, to bulk tissue e.g. in cosmetic surgery to remove wrinkles or in fistula surgery to fill the fistula channels. Depending on the intended use, absorbable materials might be used.

Film Piece Size and Shape

Film pieces are preferably in the millimeter range of 1 mm to 10 mm, not introducing much stiffness to the basic structure and having a thickness of 5 µm to 500 µm. The film pieces can have any shape, e.g. circle, oval, triangle, rectangle, square, pentagon, hexagon, cross, star.

The film piece stiffness, shape, and overall thickness, and the film piece edges could be used, additionally to the micro-protrusions, to impart additional features like palpability to facilitate orientation.

Film Piece Pattern and Spacing

Depending on the intended implant use, the film pieces might be arranged peripherally, centrally, or over the whole area. Preferably the total film area, compared to the implant face area, is less than 50%, particularly less than 25% for the total area pattern. For implants having only a central-area or peripheral film pattern, the total film area might be further reduced to geometric considerations. The film piece pattern could be used to adjust parameters like bending stiffness in different directions. Preferably the film piece pattern does not impart much stiffness to the implant to allow conformability also with uneven structures or does not negatively impact features like rolling and unrolling or folding and unfolding during laparoscopic surgery.

Film Piece Connection to Basic Structure

The film pieces can be connected to each other, in the case of a sandwich placement, and/or to the basic structure in a variety of different conventional ways, e.g., sewn, embroidered, bonded (including by thermal means), or welded thermally including ultrasonically. The welding techniques also include, in a broader sense, thermal deformation of at least one of the films (below the melting point of the film). An absorbable melt glue such as polydioxanone as a relatively low melting bioabsorbable polymer might be used as a gluing member for other film piece materials. Other soluble polymers such as polylactide, polycaprolactone or copolymers thereof might be used as solvent glues. Reactive glues like cyanoacrylates or isocyanates or oxiranes may also be used, if biocompatible.

Particularly preferred is a one-step process of micro-protrusion generation and connection to a porous tissue repair structure (basic structure). In the case of large-pore meshes, the film pieces are extending preferably over at least one part of the pore edge.

The micro-protruded film pieces are preferably enveloping/surrounding the basic structure at least in part. This helps to attach the film piece members even to low-attaching surfaces like PTFE or Polypropylene without any surface pre-treatment.

Film Piece Micro-Protrusions

The micro-protrusions (i.e., the protrusions) are solid and preferably in the range of 20 µm to 800 µm, preferably 50 µm to 500 µm, particular preferably 250 µm to 350 µm, out of the film piece area.

The micro-protrusions alter the attachment to mammalian or human soft tissue during implant placement and or ingrowths.

Micro-protrusions are protruding preferably 45° to 90° from the surface of the film pieces and could have a complex structure, like mushroom, curved rod, etc.

Preferred micro-mushrooms with a density of about 288 protrusions per $cm^2$ of film piece area were prepared. For example, mushrooms were determined by scanning electron microscopy having a height of 288 µm, a foot thickness of 410 µm diameter, a narrowed middle section of 177 µm diameter, and a head section of 410 µm diameter with a rim thickness of the mushroom head of about 12 µm.

Active Ingredients

For example, it may be advantageous to provide an implant of the present invention that has at least one biologically active or therapeutic ingredient which can optionally be released locally after the implantation. Substances which are suitable as active or therapeutic agents may be naturally occurring or synthetic, and include and are not limited to, for example, antibiotics, antimicrobials, antibacterials, antiseptics, chemotherapeutics, cytostatics, metastasis inhibitors, antidiabetics, antimycotics, gynecological agents, urological agents, anti-allergic agents, sexual hormones, sexual hormone inhibitors, haemostyptics, hormones, peptide-hormones, antidepressants, vitamins such as Vitamin C, antihistamines, naked DNA, plasmid DNA, cationic DNA complexes, RNA, cell constituents, vaccines, cells occurring naturally in the body or genetically modified cells. The active or therapeutic agent may be present in various forms, including in an encapsulated form or in an adsorbed form. With such active agents, the patient outcome may be improved or a therapeutic effect may be provided (e.g., better wound healing, or inflammation inhibition or reduction).

One preferred class of active agents is antibiotics that include such agents as gentamicin or ZEVTERA™ (ceftobiprole medocaril) brand antibiotic (available from Basilea Pharmaceutica Ltd., Basel Switzerland). Other active agents that may be used are highly effective, broad-band antimicrobials against different bacteria and yeast (even in the presence of bodily liquids) such as octenidine, octenidine dihydrochloride (available as active ingredient in Octenisept® disinfectant from Schülke & Mayer, Norderstedt, Germany), polyhexamethylene biguanide (PHMB) (available as active ingredient in Lavasept® from Braun, Switzerland), triclosan, copper (Cu), silver (Ag), nanosilver, gold (Au), selenium (Se), gallium (Ga), taurolidine, N-chlorotaurine, alcohol-based antiseptics such as Listerine® mouthwash, N a-lauryl-L-arginine ethyl ester (LAE), myristamidopropyl dimethylamine (MAPD, available as an active ingredient in SCHERCODINE™), oleamidopropyl dimethylamine (OAPD, available as an active ingredient in SCHERCODINE™ O), and stearamidopropyl dimethylamine (SAPD, available as an active ingredient in SCHERCODINE™ S), fatty acid monoesters, and most preferably octenidine dihydrochloride (hereinafter referred to as octenidine), Taurolidine, and PHMB.

One preferred class of active agents are local anesthetics that includes such agents as: Ambucaine, Benzocaine, Butacaine, Procaine/Benzocaine, Chloroprocaine, Cocaine, Cyclomethycaine, Dimethocaine/Larocaine, Etidocaine, Hydroxyprocaine, Hexylcaine, Isobucaine, Paraethoxycaine, Piperocaine, Procainamide, Propoxycaine, Procaine/Novocaine, Proparacaine, Tetracaine/Amethocaine, Lidocaine, Articaine, Bupivacaine, Dibucaine, Cinchocaine/Dibucaine, Etidocaine, Levobupivacaine, Lidocaine/Lignocaine, Mepivacaine, Metabutoxycaine, Piridocaine, Prilocalne, Propoxycaine, Pyrrocaine, Ropivacaine, Tetracaine, Trimecaine, Tolycaine, combinations thereof, e.g., Lidocaine/prilocalne (EMLA) or naturally derived local anesthetics including Saxitoxin, Tetrodotoxin, Menthol, Eugenol and pro-drugs or derivatives thereof.

Additionally, a contrast agent may be incorporated into the devices of the present invention. Such a contrast agent may be a gas or gas-creating substance for ultrasound contrast or MRI contrast, such as metal complexes like GdDTPA or superparamagnetic nanoparticles (Resovist™ or Endorem™) as taught in EP 1 324 783 B1, which is incorporated by reference. X-Ray visible substances might be included as shown in the EP 1 251 794 B1 (incorporated by reference) including pure zirconium dioxide, stabilized zirconium dioxide, zirconium nitride, zirconium carbide, tantalum, tantalum pentoxide, barium sulphate, silver, silver iodide, gold, platinum, palladium, iridium, copper, ferric oxides, not very magnetic implant steels, non-magnetic implant steels, titanium, alkali iodides, iodated aromatics, iodated aliphatics, iodated oligomers, iodated polymers, alloys of substances thereof capable of being alloyed. The contrast agents may be included in or on a mesh, or in or on the film pieces.

Basic Structure

In advantageous embodiments of the invention, the basic structure comprises a mesh-like structure having pores. The term "mesh-like structure" is to be understood rather general and includes a porous flexible sheet in general and more particularly, e.g., meshes (surgical meshes), tapes, perforated films, non-woven fabric, woven fabric, knitted sheets, knitted tapes, braided sheets, braided tapes, collageneous fibrillar sheets, mesh pouches and mesh plugs. In mesh pouches or mesh plugs, a mesh is folded or rolled and optionally fixed to itself at some points or areas, or a corresponding structure is provided from several mesh pieces. Other examples for porous basic structures are foams and sponges.

For example, the basic structure can comprise a surgical mesh having pores, wherein its first face is formed by one side of the surgical mesh. In this case, the implant can be used, e.g., for hernia repair. It is also conceivable to use the surgical implant according to the invention as, e.g., a pelvic mesh or a breast implant. In such cases, the basic structure of the implant is adapted to the desired purpose. Generally, it is not required that resorbable film pieces are attached over the entire face of the mesh-like structure or, more general, of the basic structure.

A mesh-like basic structure is preferably macro-porous with typical pore dimensions of greater than 0.5 mm, which supports good tissue integration. Other pore sizes are conceivable as well, however. As already indicated above, a mesh or mesh-like basic structure can be provided in any kind known in the art, e.g., warp-knitted or weft-knitted or crochet-knitted or woven. A design as perforated film or foil is also conceivable. Any filaments of the mesh may be bio-absorbable or non-absorbable, depending on the material. Thus, the mesh can be absorbable (resorbable), non-absorbable or partially absorbable. The filaments can be designed as mono-filaments or as multi-filaments. Tape yarns and drawn film tapes are conceivable as well. Any blends, mixtures or composites of materials and designs are also possible. Moreover, the filaments can be coated. A mesh designed as a perforated sheet is conceivable as well. Generally, the mesh-like structure is flexible and has an areal basic shape. For example, it can be based on a commercially available hernia repair mesh.

Depending upon the intended use of the tissue repair device, a biocompatible long-term-stable polymer may be used to manufacture the soft-tissue repair member (basic structure). By a long-term-stable polymer is meant a non-resorbable biocompatible polymer, or a bioabsorbable polymer which absorbs or degrades slowly, for example which possesses at least 50% of its original tearing strength in vivo 60 days after implantation. The latter group includes substances such as polyamides, which generally are regarded as resistant, as they are not designed as resorbable materials, but are attacked over time by body tissue and tissue fluids. Preferred materials for the fabric repair member include polyhydroxy acids, polylactides, polyglycolides, polyhydroxy butyrates, polyhydroxy valeriates, polycaprolactones, polydioxanones, synthetic and natural oligo- and polyamino acids, polyphosphazenes, polyanhydrides, polyorthoesters, polyphosphates, polyphosphonates, polyalcohols, polysaccharides, polyethers, cellulose, bacterial cellulose, polyamides, aliphatic polyesters, aromatic polyesters, copolymers of polymerizable substances thereof, resorbable glasses. Particularly preferred materials for the fabric repair member include polypropylene and mixtures of polyvinylidene fluoride and copolymers of vinylidene fluoride and hexafluoropropene, PTFE, ePTFE, and cPTFE, silicone, but other conventional biocompatible materials are also useful. The fabric repair members may be constructed from monofilaments, multifilaments, or combinations thereof. The fabric repair member may contain, in addition to a long-term stable polymer, a resorbable polymer (i.e., bioabsorbable or biodegradable). The resorbable and the long-term stable polymer preferably contain monofilaments and/or multifilaments. The terms resorbable polymers and bioabsorbable polymers can be used synonymously. The term bioabsorbable is defined to have its conventional meaning.

If only short-time tissue support is needed, like for fistula plugs, the fabric repair member may be manufactured from a bio-absorbable polymer or bioabsorbable polymers without any long-term-stable polymers.

Optionally the basic structure might be prepared from a biologic material such as allograft, xenograft.

Additional Layer or Layers

Tissue repair or reinforcing implants, such as meshes, may be designed to enable tissue in-growth on one side (e.g., by having open pores or interstices) and resist tissue ingrowth on the opposing side (e.g., by having a smooth surface such as a film or non-porous layer, conventionally referred to in the art as an adhesion barrier). This is important when the mesh implants are used or implanted in the abdominal area, for example in hernia repair procedures, where adhesion of the peritoneum (i.e., tissue ingrowth) to the implant is desired while tissue ingrowth or adhesions on the visceral side is unwanted (i.e., anti-adhesion). Several conventional products are known in the art and commercially available having one basically smooth side which is an adhesion barrier and one porous or rough side for tissue in-growth. The products may be completely absorbable, completely non-absorbable, or partially absorbable and partially non-absorbable. The products may be composites of multiple mesh layers and adhesion resistant barriers. Certain implants are ready for use out of the package (e.g., Proceed® Hernia Mesh, PhysioMesh®; Gore DualMesh®, and Bard Composix® Mesh) and other mesh implants are required to be pre-soaked for several minutes in water or saline solution prior to implantation in order to swell the adhesion barrier and make the implant sufficiently soft for implantation and placement in the patient (e.g., Sepramesh®; Parietex® Composite).

Additional layer/layers might be added to the surgical implant either between multiple-protruded film pieces and the basic structure or on the opposite side, or on both locations, which would result in the following assemblies:
film pieces+additional layer+basic structure or
film pieces+basic structure+additional layer or
film pieces+additional layer+basic structure+additional layer.

The additional layer or layers could have different effects on the tissue repair implant like imparting stiffness or improving tissue regeneration or ingrowth.

The additional layers that are used with surgical implant devices according to the invention should have a thickness that is sufficient to effectively prevent adhesions from forming. The thickness will typically range from about 1 µm to about 500 µm, and preferably from about 5 µm to about 50 µm. Films suitable for use include both bioabsorbable and non-absorbable films. The films are preferably polymer-based and may be made from various conventional biocompatible polymers. Non-resorbable or very slowly resorbable substances include polyalkenes (e.g. polypropylene or polyethylene), fluorinated polyolefins (e.g. polytetrafluoroethylene or polyvinylidene fluoride), polyamides, polyurethanes, polyisoprenes, polystyrenes, polysilicones, polycarbonates, polyarylether ketones (PEEKs), polymethacrylic acid esters, polyacrylic acid esters, aromatic polyesters, polyimides as well as mixtures and/or co-polymers of these substances. Also useful are synthetic bioabsorbable polymer materials, for example polyhydroxy acids (e.g. polylactides, polyglycolides, polyhydroxybutyrates, polyhydroxyvaleriates), polycaprolactones, polydioxanones, synthetic and natural oligo- and polyamino acids, polyphosphazenes, polyanhydrides, polyorthoesters, polyphosphates, polyphosphonates, polyalcohols, polysaccharides, polyethers. However, naturally occurring materials such as collagens, gelatin or natural-derived materials such as bioabsorbable omega3-fatty-acid-crosslinked gel films or oxygenized regenerated cellulose (ORC) can also be used.

The films used in surgical implant devices according to the invention may cover the entire outer surfaces of the repair fabric member (basic structure) or a part thereof. In some cases, it is beneficial to have films overlapping the borders of the repair fabric. The term border used herein means a peripheral edge or central edge if there is a hole in the mesh, e.g., for receiving an anatomical structure like the bowel for treating or preventing parastomal hernia or the spermic cord.

Porous films may be perforated before or after assembling the device, or porous films may be manufactured in such a manner that they contain pores. However, it will be appreciated by those skilled in the art that precautions have to be taken to prevent damage to other parts of the implant when perforating an assembled device.

The films can be joined together in various conventional manners, for example by sewing, gluing, welding, and laminating. The joining/connection can be about the periphery, in the center region, or over the whole assembly as a point, linear or overall connection.

Films can be connected to each other and/or to the repair fabric member (basic structure) in a variety of different conventional ways, e.g., sewn, embroidered, bonded (including by thermal means) in partial regions (e.g., in points or along lines or strips, such as the peripheral edge), or welded thermally including ultrasonically. The welding techniques also include, in the wider sense, thermal deformation of at least one of the films (below the melting point of one film). The implant can optionally have embroidered structures designed as reinforcements, e.g. rib-like structures.

A possible film-to-film connection applies heat lamination techniques, optionally by using an additional biocompatible melt glue such as polydioxanone as a relatively low-melting bioabsorbable polymer. Other soluble polymers such as polylactide, polycaprolactone or copolymers thereof might be used as solvent glues. Reactive glues like cyanoacrylates or isocyanantes or oxiranes may also be used if biocompatible.

In the following, the invention is described in more detail by means of embodiments. The drawings show in FIG. 1 an explosion view of a first embodiment of the surgical implant according to the invention, FIG. 2 a top view of a dyed film piece used in the embodiment according to FIG. 1, FIG. 3 a schematic top view of a dyed film piece used in another embodiment of the surgical implant according to the invention, FIGS. 4(a)-4(h) a three-dimensional representation of several embodiments of protrusions for film pieces of surgical implants according to the invention, FIG. 5 a top view of a further embodiment of the surgical implant according to the invention, FIG. 6 a magnified partial top view of the embodiment according to FIG. 5, in which also part of a basic structure is displayed, FIG. 7 a magnified three-dimensional representation of part of the embodiment according to FIG. 5, and FIG. 8 a schematic illustration of an embodiment of a process of manufacturing a surgical implant according to the invention, i.e. the embodiment according to FIG. 5.

FIG. 1 illustrates, in a partial explosion view, a first embodiment of a surgical implant, which is designated by 10.

The implant 10 comprises a basic structure 12, which is designed as a surgical mesh with pores 14, in the embodiment an "Ultrapro" mesh of Ethicon. "Ultrapro" is a lightweight, monofil, partially resorbable surgical mesh made of fibers of polypropylene (non-resorbable) and "Monocryl" (copolymers of glycolide and ε-caprolactone, resorbable; see above) having a pore width of about 2.27 mm in one direction and a pore width of about 3.17 mm in a direction perpendicularly thereto.

A transparent "Monocryl" film of 20 µm thickness serves as a visceral adhesion barrier sheet 16. The barrier sheet 16 is melt-fused to the basic structure 12 by means of one dyed film piece 20. In the embodiment, the dyed film piece 20 is made of a poly-p-dioxanone (PDS) sheet having an original thickness of 150 µm and being dyed with the violet dye "D&C Violet No. 2", which is well known in the art. In the view according to FIG. 1, the dyed film piece 20 is placed on top of the basic structure 12. During the melt-fusing process, the dyed film piece 20 of PDS gets soft and slightly melts so that the PDS material reaches the upper surface of the barrier sheet 16 and firmly connects it to the basic structure 12.

Figure 2:
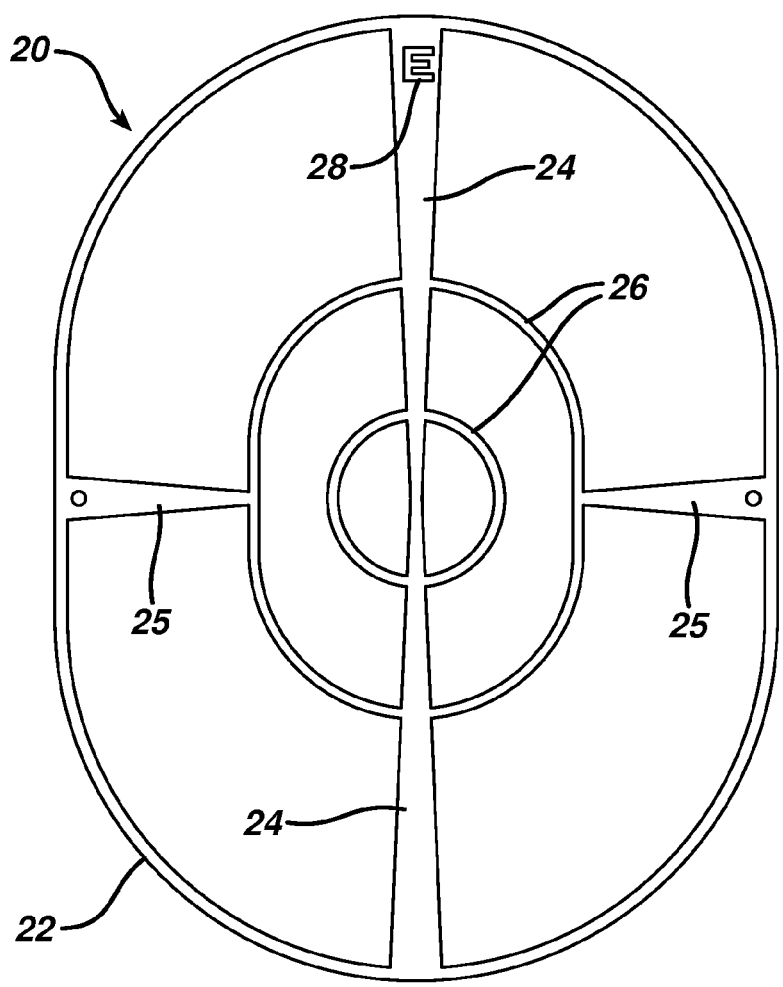

FIG. 2 shows the dyed film piece 20 in more detail. The dyed film piece 20 is coherent and is arranged in an asymmetric shape structure comprising a peripheral marking area 22, a central-axis marking area 24, a short-axis marking area 25 and two concentric inner marking areas 26. An asymmetry 28 is introduced by the letter "E". If the dyed film piece 20 is viewed upside down, the letter "E" will appear in mirror writing. Due to its violet color, the dyed film piece 20 is well visible and provides easily detectable markings to aid a surgical procedure for insertion of the implant 10. In particular, the location of the periphery, the azimuth angle orientation and the center area of the implant 10 can be readily estimated when contemplating the marking areas 22, 24/25 and 26, respectively. The letter "E" permits an easy control of the correct orientation of the barrier sheet 16, which is to be located at the downside of the implant 10.

A plurality of solid protrusions emerges from the dyed film piece 20, in the embodiment from all of its marking areas 22, 24, 25 and 26, in a direction away from the basic structure 12 and the adhesion barrier sheet 16, i.e. towards the parietal side. Examples for protrusions are described by means of FIG. 4. In FIGS. 1 and 2, the protrusions are not shown. These protrusions provide self-adhesive properties to the implant 10. Since the protrusions emerge from all areas of the dyed film piece 20, the implant 10 can be safely attached to bodily tissue in its peripheral area and in its center area. If required, the implant 10 can be peeled off after attachment, re-positioned and re-attached. General details of the protrusions are also described further above.

Thus, the dyed film piece 20 has a double function: It serves as a marker and it provides self-adhesive properties. Both effects largely facilitate the surgical procedure for placement of the implant 10.

The implant 10 may be manufactured by a method analogous to that explained further below by means of FIG. 7.

Figure 3:
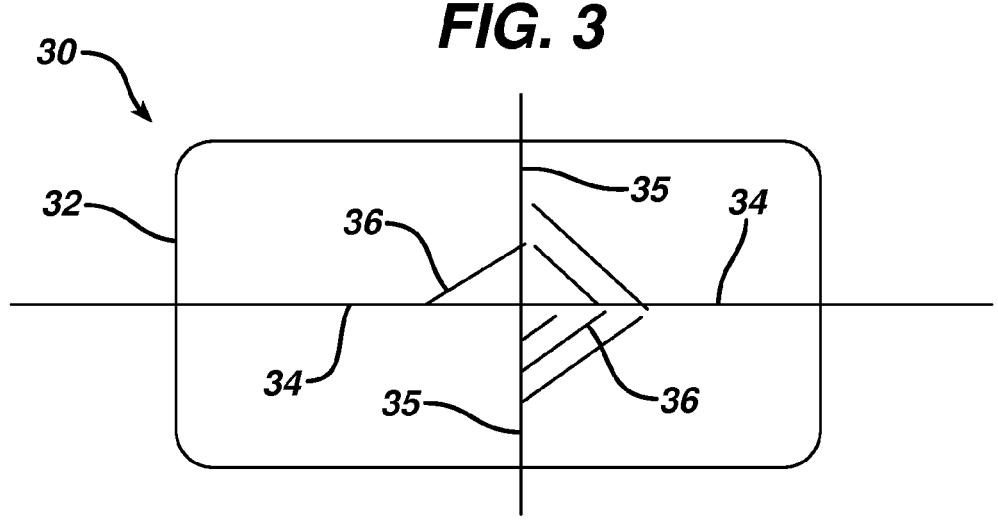
Figure 4A:
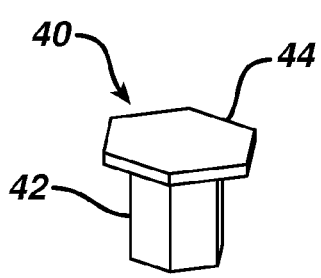
Figure 4D:
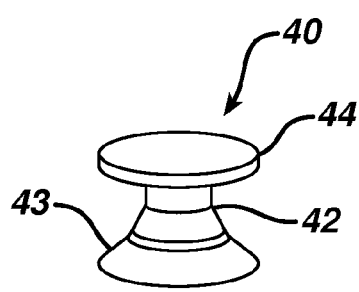
Figure 4G:
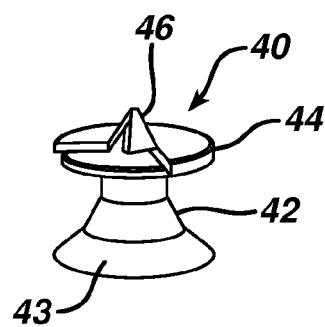
Figure 4B:
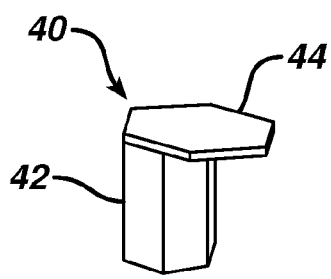
Figure 4E:
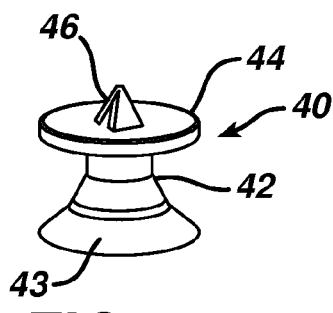
Figure 4H:
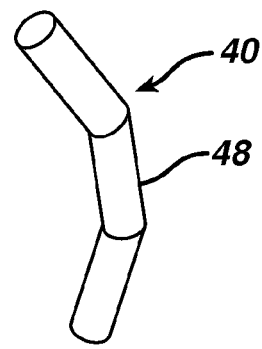
Figure 4C:
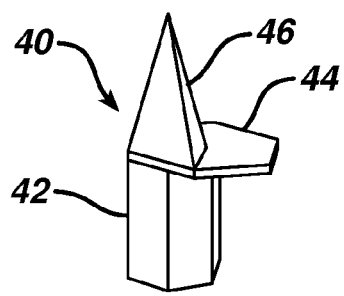
Figure 4F:
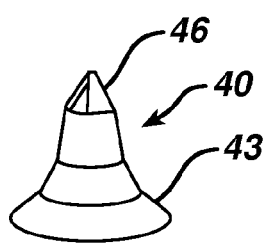

FIG. 3 illustrates a dyed film piece 30 for another implant. The dyed film piece 30 is also designed as a coherent asymmetric shape structure. Its marking areas, however, are narrower than those of the implant 10 so that the flexibility of the basic structure is less affected by the presence of the dyed film piece 30, compared to the implant 10. The markings include a peripheral marking 32, a central-axis marking 34, a short-axis marking 35, and asymmetric inner markings 36, all of them bearing protrusions facing away from the basic structure (not shown in FIG. 3).

FIGS. 4(*a*)-4(*h*), displays several types of solid protrusions, which are all designated by reference numeral 40. Most of the protrusions 40 comprise a stem 42 (some of them a stem with a pronounced foot section 43) and a head 44, which at least partially projects laterally with respect to the stem 42, see FIGS. 4(*a*) to 4(*e*) and 4(*g*). Some protrusions include a spike 46 extending beyond the head 44, see FIGS. 4(*c*), 4 (*e*) and 4(*g*). The protrusion according FIG. 4 (*f*) is completely designed as a spike. FIG. 4(*h*) shows a protrusion shaped as a bent rod 48. A particularly advantageous form is like a mushroom, see FIG. 4(*d*).

In detail: In FIG. 4(*a*), the stem 42 and the head 44 are hexagonal, with the head 44 symmetrically projecting laterally with respect to the stem 42. In FIG. 4(*b*), stem 42 and head 44 are hexagonal, while the head 44 is asymmetrically arranged with respect to the stem 42. In FIG. 4(*c*), the protrusion is similar to that of FIG. 4(*b*), but carries a trigonal pyramidal spike. The protrusion of FIG. 4(*d*) is mushroom-like and has a frusto-conical foot section 43, a tapered middle section of the stem 42 and a relatively flat head 44. In FIG. 4(*e*), the protrusion is similar to that of FIG. 4(*d*), but has an additional pyramidal spike. The protrusion of FIG. 4(*f*) comprises a circular base section 43 with a diameter decreasing down into a sharp tip or spike 46. FIG. 4(*g*) shows a mushroom-like protrusion similar to that of FIG. 4(*e*), wherein the head 44 includes some cuts. The protrusion of FIG. 4(*h*) is shaped as a bent rod 48 made of three straight sections angled with respect to each other; in a variant, it is smoothly bent along its entire length.

Typical dimensions and number densities of protrusions are disclosed further above.

Figure 5:
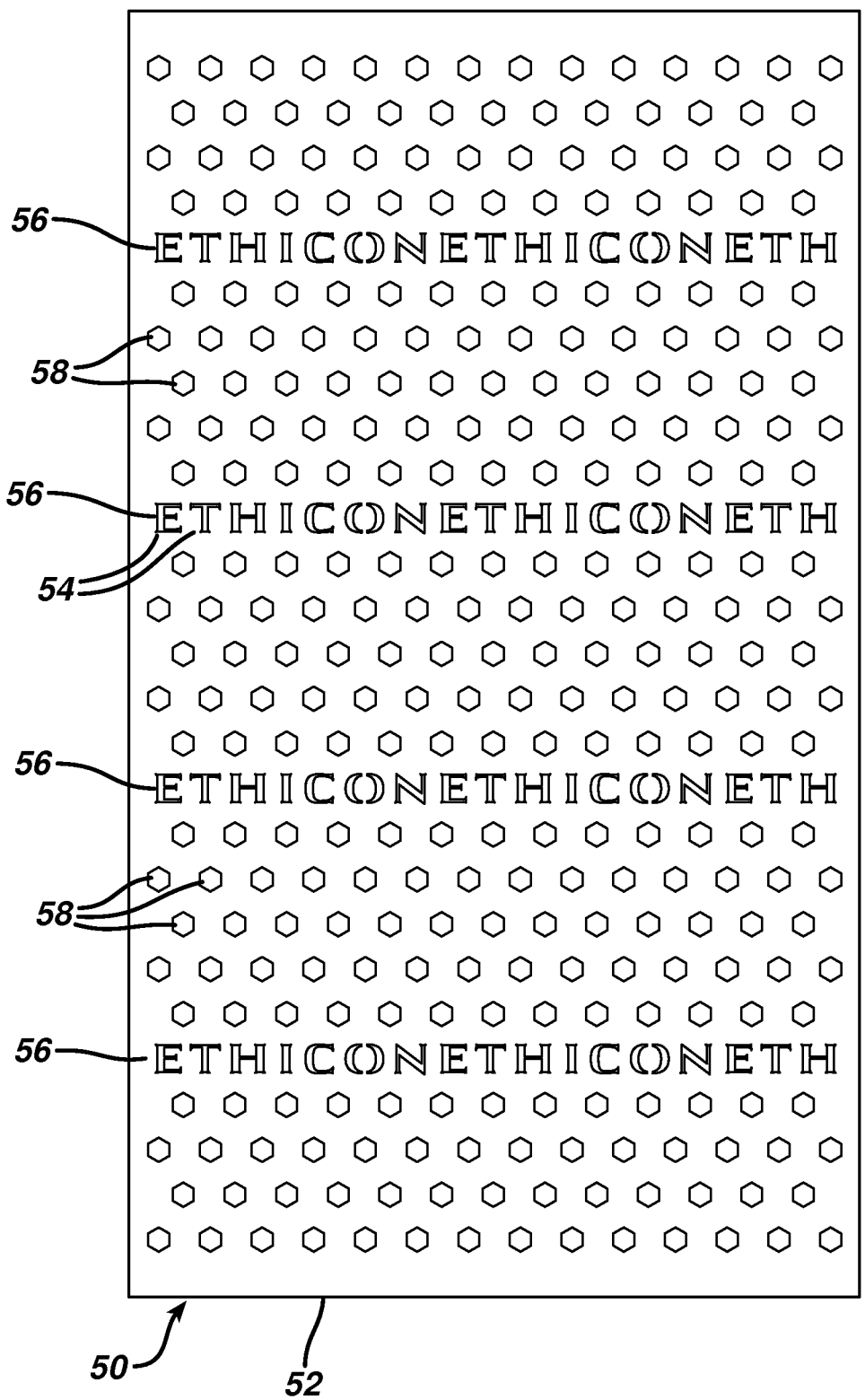

FIG. 5 shows a top view of a further embodiment of a surgical implant, which is designated by 50.

The implant 50 comprises a basic structure 52, from which FIG. 5 displays its peripheral line only. A plurality of individual dyed film pieces 54 is attached to the basic structure 52. In this embodiment, the dyed film pieces 54 are arranged in asymmetric patterns, i.e. they form several asymmetric shape structures, each one being a string of symbols 56, i.e. "ETHICONETHICONETH". Thus, each character or symbol is made up of one dyed film piece 54, except for the letter "O" which consists of two dyed film pieces, see FIG. 5. The dyed film pieces 54 are formed from dyed (violet) poly-p-dioxanone material.

In the areas between the strings of symbols 56, second film pieces 58 are attached to the basic structure 52. In the embodiment, each one of the second film pieces 58 has a hexagonal shape and is made of poly-p-dioxanone material, which is not dyed, however.

Figure 6:
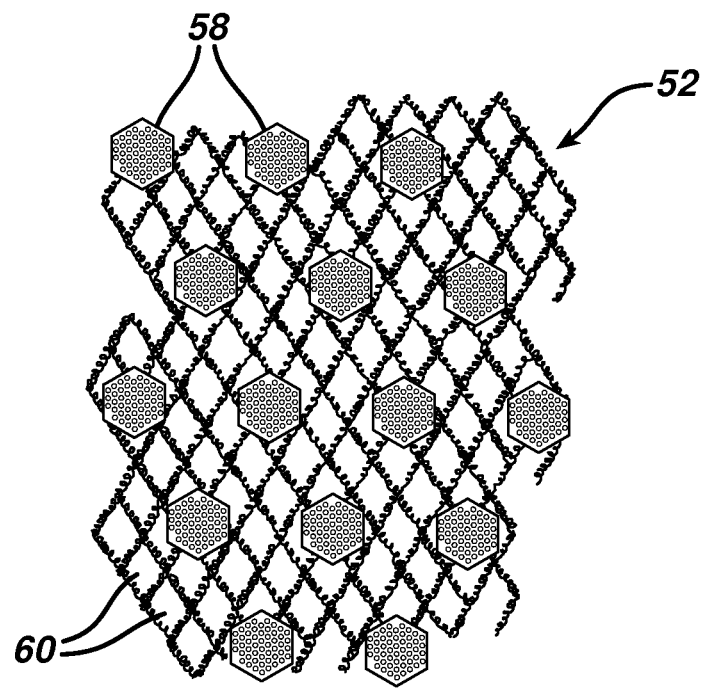

FIG. 6 schematically displays part of the second film pieces 58 and also shows the pores of the basic structure 52, which is made from a clear (undyed) lightweight polypropylene mesh.

Figure 7:
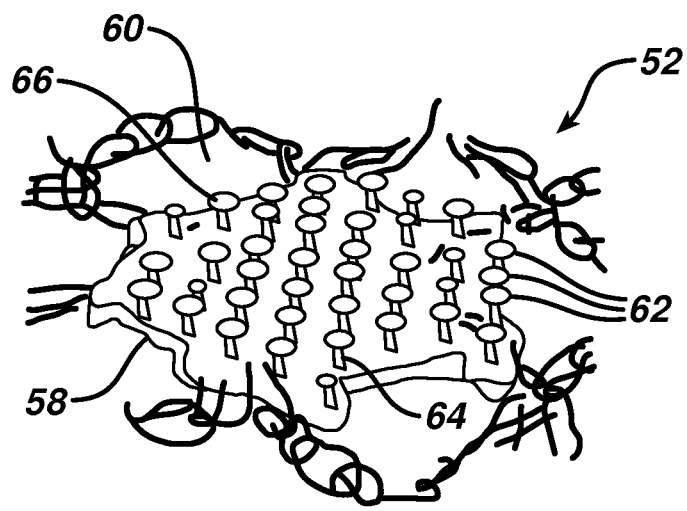

FIG. 7 illustrates that each one of the second film pieces 58 comprises a plurality of protrusions 62, which emerge in a direction away from the basic structure 52. In the embodiment, the protrusions 62 are mushroom-shaped and comprise a stem 64 and a head 66. Other shapes, like those shown in FIG. 4, are conceivable as well. Using the terminology of FIG. 5 (which is a "top" view), the protrusions 62 are pointing downwardly.

Although sheet material for the second film pieces 58 is originally placed on the "top" side of the basic structure 52, the material is drawn into the pores of the basic structure 52 during the manufacturing process (see below), and the protrusions are formed at the "bottom" side. In this way, the material of the basic structure 52 is embedded in the second film pieces 58.

The dyed film pieces 54 are provided with similar mushroom-like protrusions (not shown in the figures), which also point to the "bottom" side, and the dyed film pieces 54 enclose the material of the basic structure 52 in a similar way as the second film pieces 58 do.

The flexibility of the surgical implant 50 is mainly determined by the flexibility of its basic structure 52, because the dyed film pieces 54 and the second film pieces 58 are relatively small. The strings 56 of symbols are well visible and clearly indicate the orientation of the implant 50. Due to the protrusions 62 at the second film pieces 58 and the protrusions at the dyed film pieces 54, the implant 50 has pronounced self-attachment properties.

Figure 8:
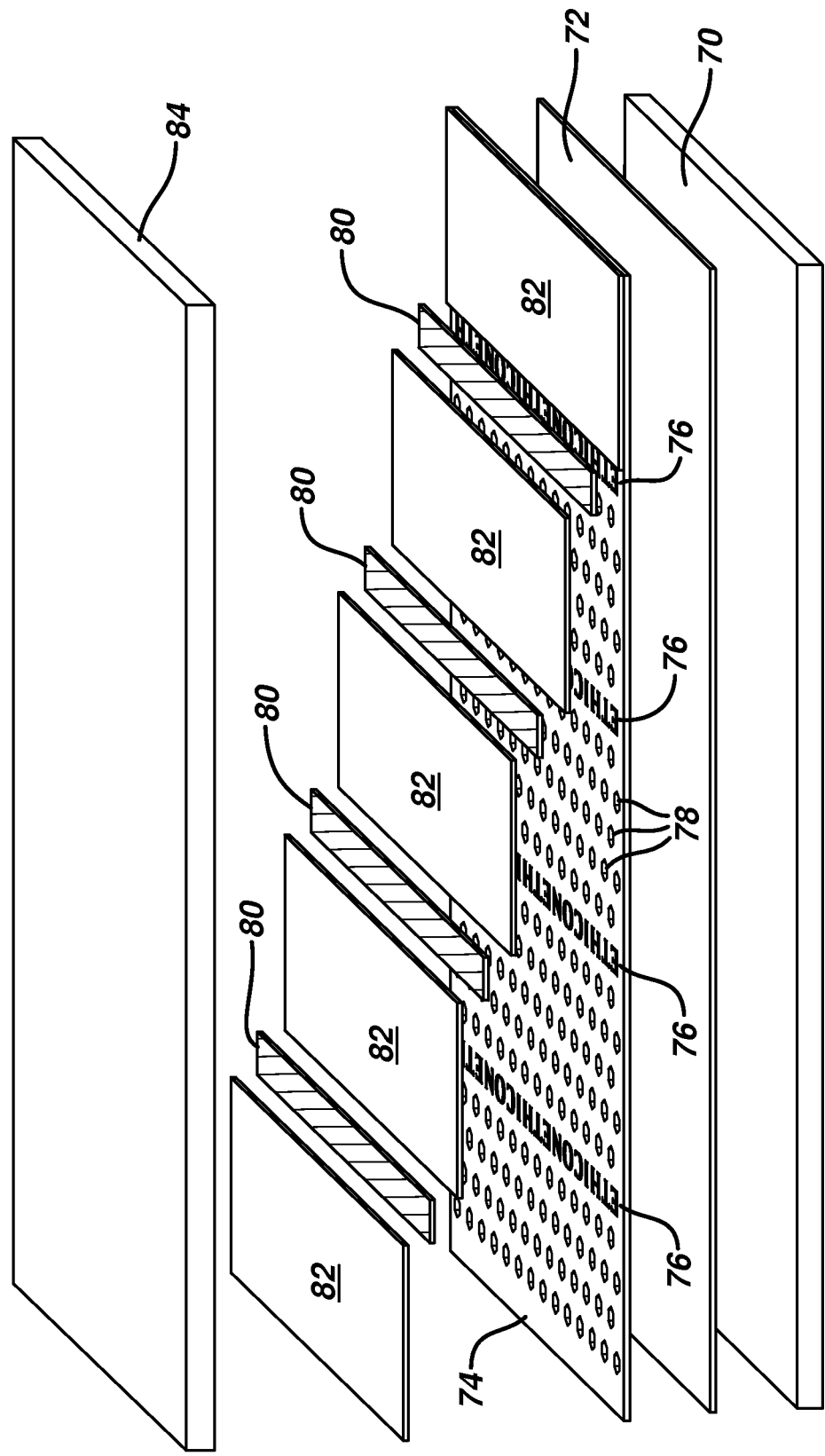

FIG. 8 schematically illustrates an embodiment of a manufacturing process of a surgical implant, i.e. a process of manufacturing the implant 50 already described by means of FIGS. 5 to 7. This process is explained by means of the following example.

In a first step, a mold 70 containing an array of cavities, each cavity having the shape of one protrusion, was made from a 2-component silicone precursor kit (elastomeric kit). In the representation according to FIG. 8, these cavities are accessible via the top side of the mold 70, but they are not shown in FIG. 8. To prepare the mold 70, a positive form (master) of polypropylene comprising on one surface, e.g., 288 mushroom-shaped protrusions/cm$^2$ with a total height of approximately 250 µm, a head diameter of approximately 375 µm, a stem diameter of approximately 200 µm and a foot diameter of approximately 340 µm was used. The liquid silicone elastomer was cast over the polypropylene master and, while keeping a horizontal position, cured at elevated temperatures (50° C. to 80° C.) in an oven for several hours. After cooling to room temperature, the silicone mold 70, comprising mushroom-shaped negatives of the protrusions, was removed from the polypropylene master.

As the basic structure of the implant, an undyed "Prolene" mesh (Ethicon) was used (surgical mesh 72, corresponds to basic structure 52 in FIG. 5), which is a non-resorbable mesh containing polypropylene fibers. The mesh could be fixated in a metal frame form to prevent movement and shrinkage.

The mold 70 was placed in a metal form with the cavities facing up, followed by the surgical mesh 72. Next, a perforated thin rubber layer serving as a mask 74 and shaped as shown in FIG. 5 was placed on top of the surgical mesh 72. The mask had opening 76 representing the strings 56 of symbols as well as hexagonal openings 78 representing the hexagonal forms of the second film pieces 58.

Sheets of material 80 (hatched) for preparing the strings 56 of symbols and sheets of material 82 for preparing the second film pieces 58 were placed side by side in an alternating manner on top of the mask 74, as shown in FIG. 8. In the example, the sheets 80 were made of dyed (violet) poly-p-dioxanone (150 µm thick), and the sheets 82 were made of undyed poly-p-dioxanone (150 µm thick). Poly-p-dioxanone has a lower melting point than the material of the surgical mesh (polypropylene).

Finally, a plate device 84 (in the example, a soft closed-cell foam material) was put on top of the sheets 80 and 82.

This assembly was placed in a heat press and allowed to heat to a temperature slightly below 130° C. for several minutes under a pressure of about 5 bar. Under these conditions, the poly-p-dioxanone material of the sheets 80 and 82 got very soft and penetrated the openings 76 and 82, respectively, in the mask 74 and the pores of mesh 72 and filled the cavities in the mold 70, i.e. those cavities not shielded by the mask 74, thus forming dyed film pieces 54 (i.e. several strings 56 of symbols) and hexagonal film pieces 58, respectively, well attached to the mesh 72 and including protrusions pointing away from the mesh 72. After cooling down the assembly to ambient temperatures (or a temperature below 50° C.), the pressure could be released, and the mold 70, the mask 74 (including the rest of the sheet material 80, 82 not used for the film pieces 54, 58) and the plate device 84 could be taken away. Because of its high flexibility, the silicone mold 70 could be removed from the protrusions without problems.

DE 10 2013 004 574 A and DE 10 2013 004 573 A disclose further examples, which can be easily adapted to the purposes of the present invention. These documents are incorporated by reference.

The invention claimed is:

1. A surgical implant, comprising
   an areal, flexible, porous basic structure having pores, a first face and a second face,
   at least one resorbable dyed film piece attached to the basic structure and comprising a plurality of solid protrusions emerging from the dyed film piece in a direction away from the basic structure, wherein the at least one dyed film piece extends into pores of the basic structure, and the protrusions emerge from the at least one dyed film piece in both directions, away from the first face of the basic structure and away from the second face of the basic structure, and wherein the at least one dyed film piece is arranged in a shape structure which is asymmetric in the area of the basic structure.

2. A surgical implant according to claim 1, characterized in that the at least one dyed film piece comprises a coherent asymmetric shape structure.

3. A surgical implant according to claim 1, characterized in that the asymmetric shape structure is formed by a plurality of individual dyed film pieces arranged in an asymmetric pattern.

4. A surgical implant according to claim 1, characterized in that, in addition to the at least one dyed film piece, second film pieces are attached to the basic structure, wherein each of the second film pieces comprises at least one protrusion emerging from the respective second film piece in a direction away from the basic structure, the second film pieces being undyed or differently dyed, compared to the at least one dyed film piece.

5. A surgical implant according to claim 1, characterized in that at least one protrusion comprises a property selected from the following list: being rod-like; being pillar-like; being mushroom-shaped; comprising a shape defined by a respective body and a respective head, the body emerging from the film piece and terminating in the head, and the head projecting laterally with respect to the body.

6. A surgical implant according to claim 1, characterized in that the asymmetric shape structure defines at least one symbol.

7. A surgical implant according to claim 6, characterized in that the asymmetric shape structure defines a string of symbols.

8. A surgical implant according claim 1, characterized in that a film is attached to the second face of the basic structure, which film comprises one feature out of each of the following groups of features: provided as single piece, provided as plurality of film pieces; being resorbable, being non-resorbable; comprising protrusions, not comprising protrusions; having barrier properties, not having barrier properties.

9. A surgical implant according to claim 8, characterized in that a film having barrier properties is attached to the second face of the basic structure, wherein this film comprises at least one of the materials selected from the following list: polyalkenes, polypropylene, polyethylene, fluorinated polyolefins, polytetrafluoroethylene, PTFE, ePTFE, cPTFE, polyvinylidene fluoride, blends of polyvinylidene fluoride and copolymers of vinylidene fluoride and hexafluoropropene, polyamides, polyurethanes, polyisoprenes, polystyrenes, polysilicones, polycarbonates, polyarylether ketones, polymethacrylic acid esters, polyacrylic acid esters, aromatic polyesters, polyimides, polyhydroxy acids, polylactides, polyglycolides, copolymers of glycolide and lactide, copolymers of glycolide and lactide in the ratio 90:10, copolymers of lactide and trimethylene carbonate, copolymers of glycolide, lactide and trimethylene carbonate, polyhydroxybutyrates, polyhydroxyvaleriates, polycaprolactones, copolymers of glycolide and ϵ-caprolactone, polydioxanones, poly-p-dioxanone, synthetic and natural oligo- and polyamino acids, polyphosphazenes, polyanhydrides, polyorthoesters, polyphosphates, polyphosphonates, polyalcohols, polysaccharides, polyethers, polyamides, aliphatic polyesters, aromatic polyesters, polyurethanes, copolymers of polymerizable substances thereof, resorbable glasses, cellulose, bacterial cellulose, allograft, xenograft, collagen, gelatin, silk.

10. A surgical implant according to claim 1, characterized in that at least two stripe-like shape structures, each comprising at least one dyed film piece and each defining a string of symbols, are attached to the basic structure and in that, optionally, second film pieces are attached to the basic structure in a region in between the stripe-like shape structures.

11. A surgical implant according to claim 1, characterized in that the surgical implant is adapted to be rolled or folded for laparoscopic placement, moved to a site of surgery through a trocar sleeve and unrolled or unfolded without sticking to itself.

12. A surgical implant according to claim 1, characterized in that the surgical implant is designed as a soft-tissue implant, preferably a hernia implant, and is adapted to fix itself at least partially in soft tissue such as muscle or fat, with the friction between the surgical implant and the soft tissue being increased in at least one direction by a factor of 2 or more, compared to a corresponding implant without protrusions.

13. A surgical implant according to claim 1, characterized in that the at least one dyed film piece comprises a material selected from the following list: synthetic bioabsorbable polymer materials, polyhydroxy acids, polylactides, polyglycolides, copolymers of glycolide and lactide, copolymers of glycolide and lactide in the ratio 90:10, copolymers of lactide and trimethylene carbonate, copolymers of glycolide, lactide and trimethylene carbonate, polyhydroxybutyrates, polyhydroxyvaleriates, polycaprolactones, copolymers of glycolide and ϵ-caprolactone, polydioxanones, poly-p-dioxanone, synthetic and natural oligo- and polyamino acids, polyphosphazenes, polyanhydrides, polyorthoesters, polyphosphates, polyphosphonates, polyalcohols, polysaccharides, polyethers, collagen, gelatin, bioabsorbable gel films cross-linked with omega 3 fatty acids, oxygenized regenerated cellulose.

14. A surgical implant according to claim 1, characterized in that the basic structure comprises at least one of the materials selected from the following list: polyalkenes, polypropylene, polyethylene, fluorinated polyolefins, polytetrafluoroethylene, PTFE, ePTFE, cPTFE, polyvinylidene fluoride, blends of polyvinylidene fluoride and copolymers of vinylidene fluoride and hexafluoropropene, polyamides, polyurethanes, polyisoprenes, polystyrenes, polysilicones, polycarbonates, polyarylether ketones, polymethacrylic acid esters, polyacrylic acid esters, aromatic polyesters, polyimides, polyhydroxy acids, polylactides, polyglycolides, copolymers of glycolide and lactide, copolymers of glycolide and lactide in the ratio 90:10, copolymers of lactide and trimethylene carbonate, copolymers of glycolide, lactide and trimethylene carbonate, polyhydroxybutyrates, polyhydroxyvaleriates, polycaprolactones, copolymers of glycolide and ϵ-caprolactone, polydioxanones, poly-p-dioxanone, synthetic and natural oligo- and polyamino acids, polyphosphazenes, polyanhydrides, polyorthoesters, polyphosphates, polyphosphonates, polyalcohols, polysaccharides, polyethers, polyamides, aliphatic polyesters, aromatic polyesters, polyurethanes, copolymers of polymerizable substances thereof, resorbable glasses, cellulose, bacterial cellulose, allograft, xenograft, collagen, gelatin, silk.

15. A surgical implant according to claim 1, characterized in that the at least one dyed film piece and the protrusions emerging therefrom are made in one piece.

16. A surgical implant according to of claim 1, characterized in that the basic structure is formed to a three-dimensional configuration, the surgical implant preferably being designed in a form selected from the following list: tubes, vascular implants, stents, breast implants, orthopaedic implants.

17. A process of manufacturing a surgical implant according to claim 1, characterized by the steps:
providing a mold containing an array of cavities, each cavity having the shape of one protrusion,
filling the mold with a fluid material forming the at least one dyed film piece and the protrusions according to a pattern defining the shape structure of the at least one dyed film piece,
hardening the fluid material,
attaching the at least one dyed film piece to a basic structure, with the protrusions pointing away from the basic structure,
removing the mold.

18. A process according to claim 17, characterized in that the mold is flexible and comprises at least one of the following materials: flexible material, silicone, polyurethane, natural rubbers, synthetic rubbers.

19. A process according to claim 17, characterized in that the pattern defining the shape structure of the at least one dyed film piece is determined by a mask placed between the basic structure and the material to be filled in the mold.

20. A process according to claim 19, characterized by the steps:
providing a layered assembly comprising, in this order:
the mold, a surgical mesh as the basic structure, the mask, a sheet of material for the at least one dyed film piece having a lower melting point than the surgical mesh, a flexible plate device,
heating the sheet of material to a temperature higher than its melting point and lower than the melting point of the surgical mesh,
pressing the mold and the plate device towards each other, whereby the material for the at least one dyed film piece is transferred through the mask into the mold and embeds the surgical mesh,
lowering the temperature and removing the mold.

21. A process according to claim 20, characterized in that the flexible plate device has one of the following properties: comprising a closed surface; being designed as a second mold, which is flexible and contains an array of cavities, each cavity having the shape of one protrusion.

22. A process according to claim 20, characterized in that second film pieces are prepared from sheet material placed side by side to sheet material used for preparing the at least one dyed film piece.

23. A process according to claim 19, characterized by the steps:

providing a layered assembly comprising, in this order: the mold, a sheet of material for the at least one dyed film piece having a lower melting point than the surgical mesh, the mask, a surgical mesh as the basic structure, a flexible plate device, heating the sheet of material to a temperature higher than its melting point and lower than the melting point of the surgical mesh, pressing the mold and the plate device towards each other, whereby the material for the at least one dyed film piece is transferred into the mold and embedded in the surgical mesh in those areas which are not shielded by the mask, lowering the temperature and removing the mold.

* * * * *